United States Patent
Kitchen et al.

(10) Patent No.: US 12,151,036 B2
(45) Date of Patent: Nov. 26, 2024

(54) ELECTRIFICATION SYSTEM FOR PREVENTING TRANSMISSION OF PATHOGENS BY DERMAL CONTACT

(71) Applicants: Grant Kitchen, Baltimore, MD (US); Luis Francisco Garcia, San Mateo, CA (US); Bill Ling, Monrovia, CA (US); Kevin Stephen McFarland, Silver Spring, MD (US); Carlos Rene Mendez, Cedar Park, TX (US); Marc Donohue, Baltimore, MD (US)

(72) Inventors: Grant Kitchen, Baltimore, MD (US); Luis Francisco Garcia, San Mateo, CA (US); Bill Ling, Monrovia, CA (US); Kevin Stephen McFarland, Silver Spring, MD (US); Carlos Rene Mendez, Cedar Park, TX (US); Marc Donohue, Baltimore, MD (US)

( * ) Notice: Subject to any disclaimer, the term of this patent is extended or adjusted under 35 U.S.C. 154(b) by 797 days.

(21) Appl. No.: 17/146,476

(22) Filed: Jan. 11, 2021

(65) Prior Publication Data

US 2021/0213146 A1    Jul. 15, 2021

Related U.S. Application Data

(60) Provisional application No. 62/959,547, filed on Jan. 10, 2020.

(51) Int. Cl.
*A61L 2/03*  (2006.01)
*A61L 2/26*  (2006.01)
(Continued)

(52) U.S. Cl.
CPC ............. *A61L 2/03* (2013.01); *A61L 2/26* (2013.01); *A61N 1/0484* (2013.01); *A61N 1/32* (2013.01);
(Continued)

(58) Field of Classification Search
CPC .................................. A41D 13/1192
See application file for complete search history.

(56) References Cited

U.S. PATENT DOCUMENTS 3,417,413 A     12/1968   Gage
4,765,343 A  *   8/1988   Brenman ............... A61B 5/332
                                                    600/384

(Continued)

FOREIGN PATENT DOCUMENTS

CN           201612160 U  * 10/2010
DE      102016224568 A1  *  6/2018
(Continued)

OTHER PUBLICATIONS

Sen et al., Electroceutical Fabric Lowers Zeta Potential and Eradicates Coronavirus Infectivity upon Contact, doi.org, May 15, 2020.
(Continued)

*Primary Examiner* — Michael W Kahelin
*Assistant Examiner* — Luke M Stanley

(57) ABSTRACT

An electrification system is used to prevent the transmission of pathogens by dermal contact. The electrification system includes a skin-bracing object, a power supply, and at least one resistor. The skin-bracing object includes an object body and a conductive feature. The skin-bracing object is an object that regularly comes into physical contact with a user's skin. The object body is the structure of the skin-bracing object and can be, but is not limited to, a pillowcase, a bed sheet, a bed pad, a blanket, a piece of medical gauze, a face mask, a set of medical scrubs, or a food preparation surface. The power supply, the resistor, and the conductive feature are electrically connected in series to each other. Thus, the conductive feature carrier an electrical current to electrify pathogens that come into physical contact with the conductive feature.

15 Claims, 3 Drawing Sheets

(51) Int. Cl.
*A61N 1/04* (2006.01)
*A61N 1/32* (2006.01)

(52) U.S. Cl.
CPC ........ *A61L 2202/11* (2013.01); *A61L 2202/26* (2013.01); *A61N 1/0468* (2013.01)

(56) References Cited

U.S. PATENT DOCUMENTS

| | | |
|---|---|---|
| 5,107,620 A | 4/1992 | Mahan |
| 6,979,491 B2 | 12/2005 | Yan et al. |
| 8,546,474 B2 | 10/2013 | Saint-Jalmes et al. |
| 10,813,355 B2 | 10/2020 | Zwiebel et al. |
| 10,870,741 B2 | 12/2020 | Ahmad |
| 2004/0121077 A1 | 6/2004 | Park et al. |
| 2007/0239212 A1* | 10/2007 | Schneider ............ A41B 11/005 607/2 |
| 2010/0100997 A1* | 4/2010 | Lee .................... H01R 13/2407 428/156 |
| 2010/0312293 A1 | 12/2010 | Skiba et al. |
| 2011/0142898 A1 | 6/2011 | Fan |
| 2012/0165831 A1 | 6/2012 | Gonzalez |
| 2016/0010273 A1* | 1/2016 | Ashayer-Soltani ........................ D06M 15/285 428/221 |
| 2017/0056536 A1* | 3/2017 | Hallab .................... A61F 2/482 |
| 2017/0266446 A1* | 9/2017 | O'Clock ............ A61N 1/36034 |
| 2020/0157709 A1 | 5/2020 | Kanematsu et al. |
| 2020/0222687 A1* | 7/2020 | Skiba ..................... A61N 1/205 |

FOREIGN PATENT DOCUMENTS

| | | | |
|---|---|---|---|
| WO | WO2014178943 A1 | 11/2014 | |
| WO | WO-2018075893 A1 * | 4/2018 | ....... A61F 13/00008 |

OTHER PUBLICATIONS https://www.youtube.com/watch?v=B7TpMrJy8wg&feature=emb_logo&ab_cha.

* cited by examiner

ELECTRIFICATION SYSTEM FOR PREVENTING TRANSMISSION OF PATHOGENS BY DERMAL CONTACT

The current application claims a priority to the U.S. Provisional Patent application Ser. No. 62/959,547 filed on Jan. 10, 2020. The current application is filed on Jan. 11, 2021, while Jan. 10, 2021 was on a weekend.

FIELD OF THE INVENTION

The present invention generally relates to the application of an electrical current to maximize hygiene and exploit the regenerative potential of microcurrents on the dermis. More specifically, the present invention can be used in making bedding-related items for acne treatment or alleviation of pressure sores and can be expanded to other fields including as medical gauze and food preparation surfaces.

BACKGROUND OF THE INVENTION

Bacteria are implicated in the development of many medical issues, including acne, pressure sores, forms of dermatitis, and diseases from ingestion. Over the years, various antimicrobial techniques have been developed to sterilize surfaces or materials. Although methods such as heating in an autoclave or irradiation with ultraviolet light guarantee sterility, such extreme conditions are not adaptable for a clinical or home setting. As a result, chemical methods arose as popular alternatives due to their activity in ambient conditions. However, nature is inherently adaptive and genetic mutations soon arose that conferred resistance to antibiotics. Currently, antibiotic resistant bacteria are a major issue in hospitals.

It is possible to combat such bacteria using metals with antimicrobial properties such as silver, copper, and zinc. Although the mechanism of action remains unknown, it is likely that the metals assist with the generation of reactive oxygen species. These radical species are powerful oxidants with the ability to damage nucleic acids, amino acids, lipids, and other compounds within the cell. Perhaps the most prominent effect of this is the destabilization and subsequent permeation of the membrane. Additionally, metal ions can bind to sulfur groups on proteins, altering their stability and function. As a result, such metals are a broad-spectrum antibiotic with some antiviral and antifungal properties.

Despite the wide applicability of these metals, their mechanism of action is passive and slow, usually taking hours to eliminate microbes. A faster alternative is treatment with electrical currents as low as 200 nanoampere (nA). As a point of comparison, the sensitivity threshold for human skin is approximately 10 milliampere (mA), and currents above 100 mA can be lethal. The mechanism of such treatment draws from the microbiological technique of electroporation, in which the application of low-current electrical pulses induces reversible breakdown of the cell membrane. Prolonged treatment can perforate the bacteria to the point of death.

A surface that can hold sterility without sizeable equipment has a multitude of applications, particularly at home and in hospitals. Acne, for example, is caused by the proliferation of certain bacteria within clogged skin pores. Treatments typically involve cleansing the face with a bactericide such as benzoyl peroxide. Likewise, bacterial biofilms are a leading cause of complications from pressure ulcers, or bedsores. An electrified cloth can replace the harsh antibiotic treatments necessary to treat such conditions. Additionally, studies have shown that electric stimulation of dermal wounds accelerates regeneration rate. The combination of metal inhibition, electrical inhibition, and stimulated wound healing provide a distinct advantage over previous conceptions of antimicrobial surfaces.

Therefore, the objective of the present invention is sustaining a low current uniformly across a surface as an effective method of sterilization. Instances where the present invention is applied to healthcare products, another advantage of the present invention is the electrical stimulation of wound healing and regeneration. In the preferred embodiment of the present invention, electrical sterilization is compounded by the presence of silver nanoparticles which confer broad spectrum, passive microbial resistance and electrical conductivity to fabric into which they are embedded. By sterilizing areas of the skin in close contact with the fabric, such an embodiment alleviates bacterially exacerbated conditions such as acne or pressure ulcers.

SUMMARY OF THE INVENTION

The present invention provides a pathogen-free surface that is safe for topical use, is washable, and confers broad-spectrum antiseptic activity. For the purpose of the present invention, a surface refers to a one-dimensional plane of either natural or synthetic fabrics or a uniform layer of liquid capable of carrying an electric current.

For the present invention as an electrified cloth, the surface can contain metal nanoparticles and other conductive organic or synthetic materials that confer antiseptic properties. The particles are adhered to the fabric on the surface and, when coupled with an electrical current, contribute to the antimicrobial and wound healing effects. Fibers of the fabric are made of cotton, linen, silk, wool, leather, blending fabric, synthetic fibers, or a combination therein. The fabric can be either in its natural color or dyed with various colors without losing antimicrobial properties. The surface of the present invention is non-toxic, safe, and environmentally friendly and is thus suitable for use in medical, healthcare, or household related purposes. The electrified surface is versatile and can be used as a bandage, gauze, surgery cloth, or even as a hygienic surface for food preparation domestically or industrially. It can also be used in making articles of clothing including undergarments, cushions, shoe insoles and lining, and external feminine hygiene products. The term "antimicrobial" as used in the context of "anti-microbial surface," in the present invention means that the conductive surface demonstrated antibacterial, and antifungal properties by killing and/or suppressing growth of pathogenic organisms such as, but not limited to, antibiotic resistant *Escherichia coli*, gram positive and negative bacteria, and many types of fungi.

For the present invention as a food preparation surface, the surface is a porous material that sufficiently allows fluids to form a contiguous layer capable of carrying a current across that material. This surface will have an embedded circuit, which provides a constant current source once a layer of fluid is uniformly dispersed between the electrodes. The fluid may contain different types of solutes dissolved in it, including but not limited to salts, metals, ions, or other conductive particles (or lack of any thereof) which renders the surface conductive.

DETAILED DESCRIPTION OF THE INVENTION

All illustrations of the drawings are for the purpose of describing selected versions of the present invention and are not intended to limit the scope of the present invention.

Figure 1:
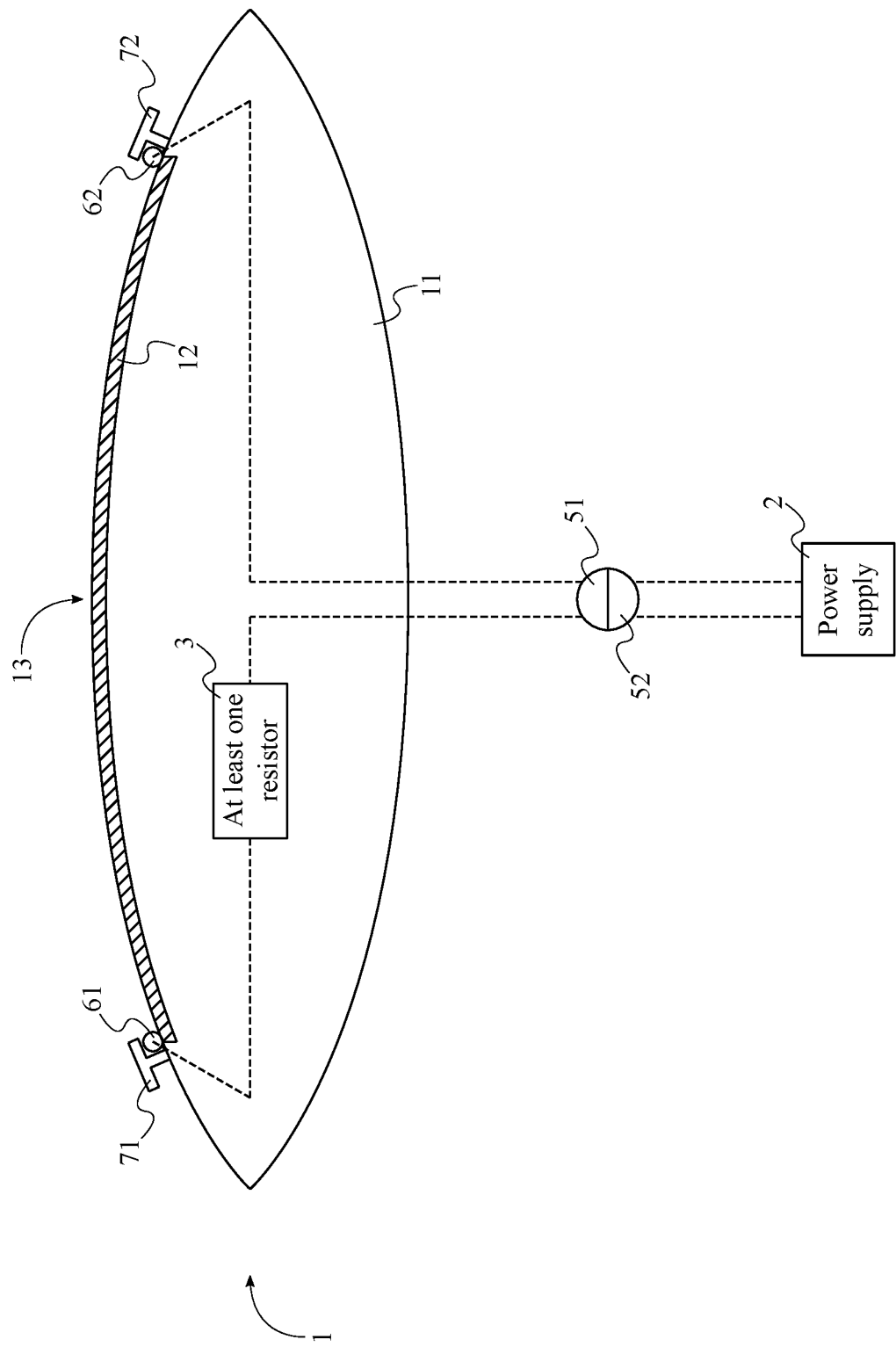
FIG. 1 is a schematic side view illustrating an exemplary embodiment of the present invention, wherein the skin-bracing object is configured as a pillowcase in the exemplary embodiment.
Figure 2:
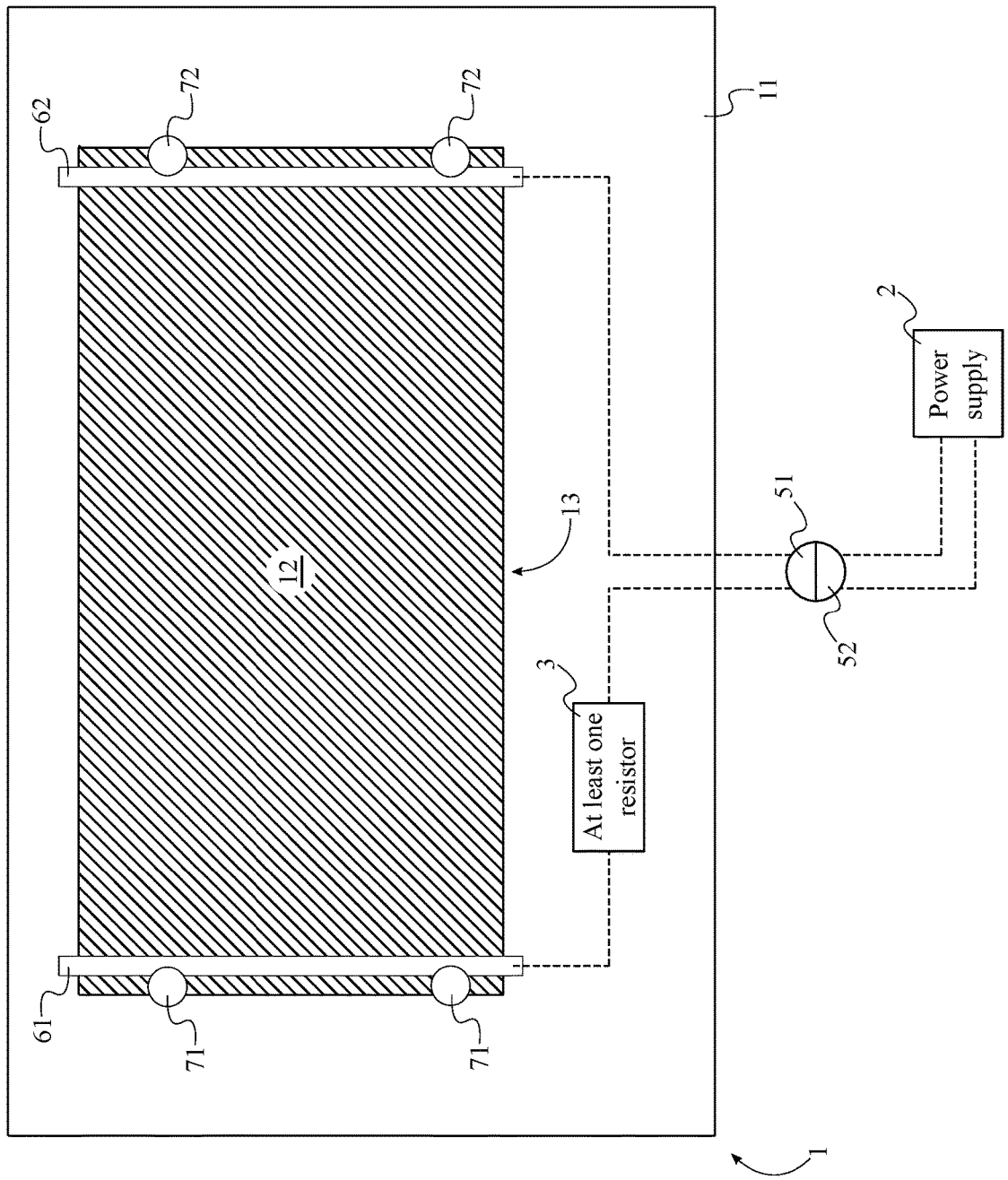
FIG. 2 is a schematic top view illustrating the exemplary embodiment of the present invention.

The present invention is an electrification system for preventing transmission of pathogens by dermal contact. The present invention allows a user's skin to remain in physical contact with an object without transmitting pathogens from the object to the user's skin or vice versa. The pathogens can be, but are not limited to, bacteria, fungi, viruses, or combinations thereof. Thus, a preferred embodiment of the present invention comprises a skin-bracing object 1, a power supply 2, and at least one resistor 3, which are shown in FIGS. 1 and 2. The skin-bracing object 1 is any object that regularly makes physical contact with a user's skin. In addition, the skin-bracing object 1 comprises an object body 11 and a conductive feature 12. The object body 11 is the physical structure of the skin-bracing object 1. The conductive feature 12 is used to eradicate pathogens that come into physical contact with conductive feature 12. Moreover, the power supply 2 is used to apply an electrical current across the conductive feature 12, which consequently eradicates pathogens by electrifying them. The power supply 2 can be, but is not limited to, a portable power source (e.g., a generator, a battery, a solar assembly, etc.) or a power cord that is plugged into an electrical outlet. The at least one resistor 3 is used to appropriately restrict an electrical current through the present invention in order to prevent the short circuit of any electrical components of the present invention.

Figure 3:
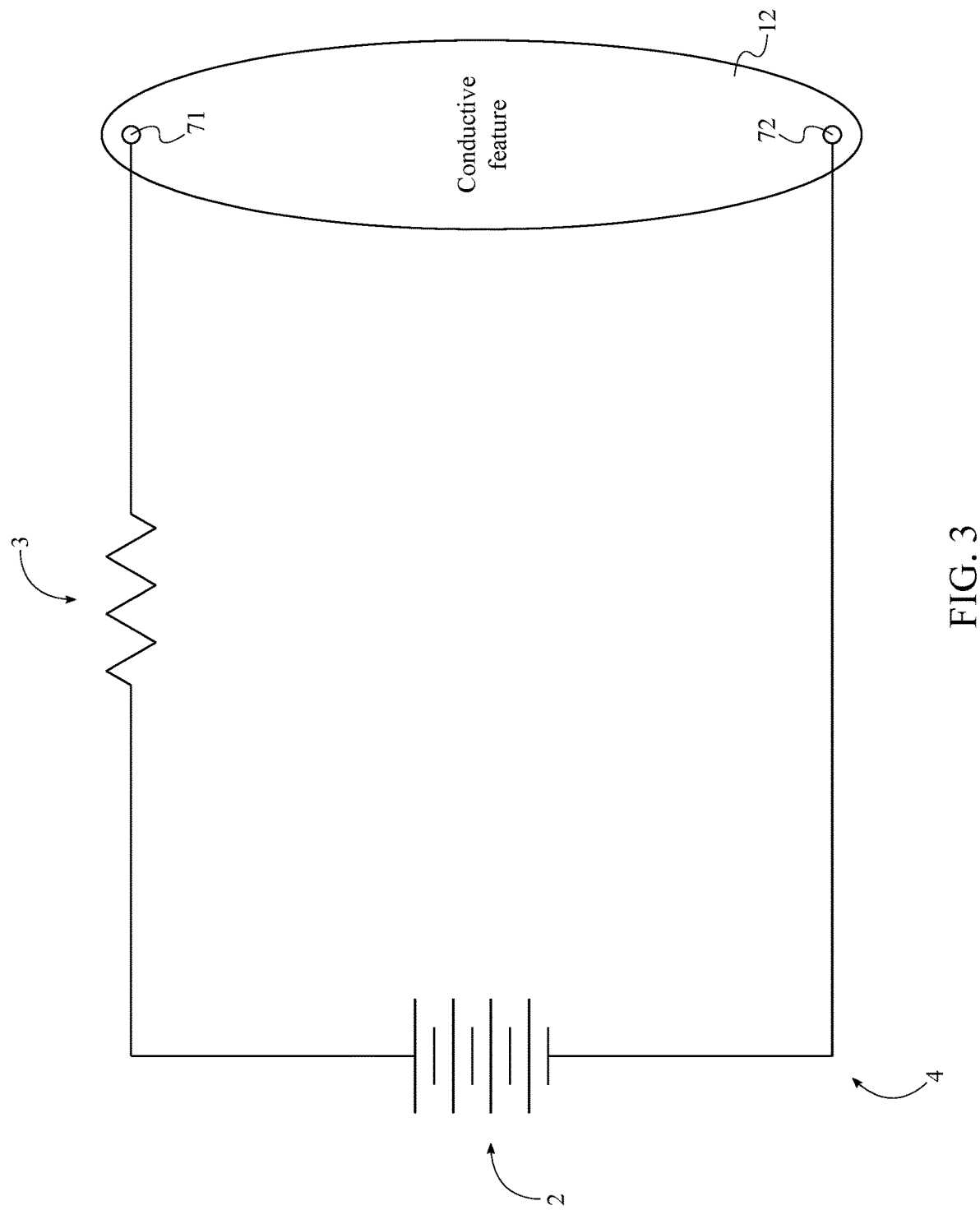
FIG. 3 is a circuit diagram illustrating the closed circuit for the present invention.

The general configuration of the aforementioned components allows the present invention to efficiently and effectively prevent transmission of pathogens by dermal contact. The conductive feature 12 is integrated into at least one specific surface 13 of the object body 11, which allows the specific surface 13 to be electrified by the conductive feature 12. Furthermore, the specific surface 13 is located where the skin-bracing object 1 actually makes physical contact with a user's skin. The at least one resistor 3 is mounted onto the object body so that the at least one resistor is properly secured to the skin-bracing object 1. In order to electrify the conductive feature 12, the conductive feature 12, the at least one resistor 3, the power supply 2 are electrically connected in series to each other as a closed circuit 4, which is shown in FIG. 3, so that no other biological matter (e.g., an insect or a portion of a user's skin) is needed to complete an electrical circuit between the conductive feature 12 and the power supply 2. Consequently, the power supply 2 is configured to electrify pathogens in physical contact with the specific surface 13 by applying a specified current through the conductive feature 12. The specified current is optimized to eradicate a larger quantity of pathogens while minimizing the required time and the required power to do so. In addition, the specified current is set to be less than a current threshold of human sensitivity so that the present invention can electrify pathogens while going unnoticed by a user of the skin-bracing object 1. In the preferred embodiment of the present invention, the current threshold of human sensitivity is set to be approximately 50 milliampere (mA). In reference to the aforementioned current threshold, the term "approximately" preferably means within an error range of up to ±5 mA. Moreover, the specified current needs to be greater than 200 nanoamperes (nA), which is the minimum effective current to electrify pathogens with the present invention.

The skin-bracing object 1 is preferably a textile that readily adjusts to the contours of a user's skin. The textile can be, but is not limited to, a knitted fabric, a spun fabric, a woven fabric, or a nonwoven fabric. This allows for some useful embodiments of the object body 11, which include, but are not limited to, a pillowcase, a bed sheet, a bed pad, a blanket, a piece of medical gauze, a face mask, and a set of medical scrubs. As one example, if the object body 11 is a bedsheet, then the present invention be used to electrify the specific surface 13 and prevent bedsores because a user's bedsore can be the site of a bacterial infection resulting from the physical contact between the bedsheet and the user's skin. As another example, if the object body 11 is a medical gauze, then the present invention be used electrify the specific surface 13 and disinfect an open wound, which would reduce the risk of a bacterial infection at the open wound. As another example, if the object body 11 is a facemask, then the present invention be used electrify the specific surface 13 and prevent acne because a user's acne can be the site of bacterial infection resulting from the physical contact between the facemask and the user's pores.

The conductive feature 12 can be configured into a variety of different embodiments. One embodiment of the conductive feature 12 is exclusively a plurality of conductive fibers. These conductive fibers can be knitted, spun, woven, or integrated into a portion of the object body 11 that corresponds to the specific surface 13. These conductive fibers can also be made of an organic conductive material or a conductive metal. Another embodiment of the conductive feature 12 is a blend of conductive fibers and insulative fibers. Similar to the previous embodiment, the conductive fibers and insulative fibers in this blend can be knitted, spun, woven, or integrated into a portion of the object body 11 that corresponds to the specific surface 13. The conductive fibers in this blend can also be made of an organic conductive material or a conductive metal. Another embodiment of the conductive feature 12 is a plurality of insulative fibers with conductive nanoparticles, wherein the conductive nanoparticles are impregnated along each of the plurality of insulative fibers. Similar to the previous embodiments, these insulative fibers can be knitted, spun, woven, or integrated into a portion of the object body 11 that corresponds to the specific surface 13. This plurality of insulative fibers is preferably made of cotton, while these conductive nanoparticles are preferably made of silver for an additional antiseptic benefit but can alternatively be made of stainless steel, gold, or any other kind of conductive metal. In addition, these conductive nanoparticles are 33 percentage by weight (wt. %) of the conductive feature 12. Another embodiment of the conductive feature 12 is a plurality of insulative fibers with a conductive surface treatment, wherein the conductive surface treatment is applied to each of the plurality of insulative fibers. Similar to the previous embodiments, these insulative fibers can be knitted, spun, woven, or integrated into a portion of the object body 11 that corresponds to the specific surface 13. The conductive surface treatment can be made of stainless steel, silver, gold, or any other kind of conductive metal and can be applied with methods including, but not limited to, electro-deposition and vapor-deposition.

The specified current can be modified by the power supply 2 in order to better electrify pathogens in physical contact with the specific surface 13. This is done by using a pulsed direct current (DC) or an alternating current (AC), both of which have been experimentally proven to be better at sterilization than using a straight DC. Thus, one embodiment of the power supply 2 is configured to apply the specified current as an AC, and a frequency of the AC is set to be approximately 1.8 Hertz (Hz). However, further study is required to find a more optimal frequency of the AC. In addition, an alternative embodiment of the power supply 2 is configured to apply the specified current as a pulsed DC, and a frequency of the pulsed DC is set to be approximately 1.8 Hz. However, further study is required to find a more optimal frequency of the pulsed DC. Moreover, the pulsed DC can range between 1 mA to 9 mA. In reference to the aforementioned frequencies, the term "approximately" preferably means within an error range of up to +0.5 Hz.

When the skin-bracing object 1 is a textile and needs to be washed, the skin-bracing object 1 needs to be able to electrically disconnect from the power supply 2. Thus, as can be seen in FIGS. 1 and 2, the present invention may further comprise a first electrical connector 51 and a second electrical connector 52, which are interlocking components that can be selectively engaged to each other or can be selectively disengaged from each other. The first electrical connector 51 is preferably a pair of banana plugs, while the second electrical connector 52 is preferably a female connector that is integrated into a portable power source, which would be acting as the power supply 2. In addition, the resistor 3 and the conductive feature 12 are electrically wired to the first electrical connector 51, which allows the resistor 3 and the conductive feature 12 to readily form an electrical connection with the power supply 2. Likewise, the power supply 2 is electrically wired to the second electrical connector 52, which allows the power supply 2 to readily form an electrical connection with the resistor 3 and the conductive feature 12. The first electrical connector 51 is detachably and electrically engaged to the second electrical connector 52 so that the closed circuit 4 is completed between the resistor 3, the conductive feature 12, and the power supply 2 while using the present invention to electrify pathogens.

In order to effectively carry an electrical current across the conductive feature 12, the present invention may further comprise a first electrical terminal 61 and a second electrical terminal 62, which are shown in FIGS. 1 and 2. As can be seen in FIG. 2, the first electrical terminal 61 and the second electrical terminal 62 are preferably a pair of exposed parallel wires. The first electrical terminal 61 and the second electrical terminal 62 are mounted onto the object body 11 so that the first electrical terminal 61 and the second electrical terminal 62 are properly secured to the skin-bracing object 1. The first electrical terminal 61 and the second electrical terminal 62 are positioned opposite to each other across the specific surface 13, which allows an electrical current to be carried from one side of the conductive feature 12 to the other side of the conductive feature 12, while leaving enough room in between the first electrical terminal 61 and the second electrical terminal 62 for a user's skin to easily make physical contact with the conductive feature 12. More specifically, if the skin-bracing object 1 is a textile, then the first electrical terminal 61 and the second electrical terminal 62 can be ergonomically embedded into the seams of the textile, which would reduce or prevent any tactile discomfort endured by a user bracing the present invention. In order to complete the closed circuit, the resistor 3 needs to be electrically connected to the conductive feature 12 through the first electrical terminal 61, and the power supply 2 needs to be electrically connected to the conductive feature 12 through the second electrical terminal 62. Furthermore, the present invention may further comprise at least one first insulative rivet 71 and at least one second insulative rivet 72, which are respectively used to mount the first electrical terminal 61 and the second electrical terminal 62 to the object body 11 without creating any electrical interference for the closed circuit 4. Thus, the first electrical terminal 61 is pressed against one side of the conductive feature 12 by the first insulative rivet 71, while the second electrical terminal 62 is pressed against the other side of the conductive feature 12 by the second insulative rivet 72 so that the first electrical terminal 61 and the second electrical terminal 62 make the necessary physical contact with the conductive feature 12 in order to induce an electrical current through the closed circuit 4.

Supplemental Description

The present invention provides an antimicrobial surface comprises a conductive fabric or surface that carries a microcurrent as a novel method of sterilization. The surface can be comprised any surface capable of carrying a charge, such as, but not limited to, any fabrics that are woven, knitted, spun, or unwoven, and which have been rendered conductive by using conductive fibers, blends of conductive and nonconductive fibers, impregnation of non-conducting fibers with metal nanoparticles, or other surface treatments of non-conducting fibers. These materials also include porous and nonporous natural or synthetic surfaces that can trap fluid within it to allow a current to conduct throughout the surface.

Alternating current and direct current both kill bacteria, allowing for a multitude of voltage sources. In the preferred embodiment of the invention, current is provided by a detachable power cell in order to make the product washable. The power cell is connected to the circuit via banana plugs, with the female connector integrated into the power cell to eliminate areas where water can collect and cause damage. The male connectors are attached to the ends of highly conductive wiring, preferably braided stainless-steel wiring to limit oxidation and promote flexibility.

For the present invention as the proposed fabric design, the full circuit can be visualized as a wire circuit embedded into the seams of bedding items such as a pillowcase. Wiring on the shorter edge is removed to render the circuit incomplete, while the battery pack is attached along the opposite edge. Any wiring on this edge is insulated to prevent the formation of localized currents. The wiring on the longitudinal edges is exposed and sewn tightly into the seams. Plastic, non-conducting rivets may also be used to anchor the wire such that there is maximal contact between wire and fabric. In this way, conductive fabric completes the circuit between the exposed parallel wires, allowing a constant, uniform current to flow across the surface. A resistor appropriate for the fabric size and voltage source restricts the current amperage to less than 10 mA but more than 200 nA. For the examples presented here, a 33 wt. % silver-impregnated cotton was used, as the silver confers additional antimicrobial properties. However, it is feasible to use other fabrics so long as they can carry a current.

For the present invention as the proposed fluid design, the full circuit can be visualized as a wire circuit embedded within or onto a non-conductive housing. Within the housing, a detachable battery pack or a relay switch is attached to render the circuit incomplete during storage. Any wiring embedded on the housing is insulated to prevent the formation of localized currents or short circuits. The wiring on the longitudinal edges is exposed to the fluid layer. In this way, a layer of conductive fluid completes the circuit between the exposed parallel electrodes, allowing a constant, uniform current to flow across the surface. A resistor appropriate for the surface size and voltage source restricts the current amperage to less than 10 mA but more than 200 nA. For the examples presented here, a porous bamboo surface was used. However, it is feasible to use other materials so long as they can carry a current.

Besides bedding and food preparation surfaces, a salient application of this device is in the field of medical gauze. From literature, it is known that microcurrents stimulate regeneration of wounds and can be extremely beneficial to burn victims, for example. In this case, we cannot use the aforementioned power cell and wiring because they restrict movement and product flexibility. A potential solution may be to use button cell batteries with a printed circuit.

In addition to the embodiments previously described, there exist many alternatives regarding specific components. For example, the identity of the metal can change without altering the overall function of the device. Additionally, the device can function with other fabrics that are not impregnated with nanoparticles, such as conductive fibers or a blend of conductive fibers, or fibers that are otherwise rendered conductive.

For some examples, the following bacterial viability experiments were conducted using: 1) *E. coli* strain DH5α, a genetically engineered strain with resistance to the antibiotic ampicillin; 2) *Bacillus subtilis*, a gram-positive bacterium, cultured off a human face; and 3) *Saccharomyces cerevisiae*, otherwise known as yeast.

A first example is an assessment of electrification as a means of bacterial inhibition. To verify the effectiveness of current as a bacterial growth inhibitor, a circuit comprising of a battery, sterile aluminum strips of uniform size, and a resistor was made. Alligator clips and copper wire were used to connect and complete the circuit. After checking for current with a multimeter, 100 μL of bacterial suspension was added onto the aluminum strips. The strips were electrified at currents of 2 mA and 9 mA for periods of five minutes, ten minutes, fifteen minutes, and 24 hours. Following electrification, the strips were streaked onto LB agar plates previously treated with ampicillin, then incubated at 37° C. for 12 hours to check cell viability. A set of non-electrified controls were also performed in parallel under the same conditions. Triplicates of all experimental conditions were taken. Effects on bacterial viability were determined by qualitatively comparing the electrified trials against the controls.

A second example is for the viability of fabrics in the circuit. To test that a fabric could create a uniformly charged surface, a circuit was built as in the first example using a conductive fabric to complete the circuit. Specifically, it was assessed that the ability of cotton impregnated with silver nanoparticles, cotton interwoven with stainless steel strands, and polyester with carbon fibers to conduct uniformly. Once the circuit was constructed with a single square of fabric (4 cm×4 cm), a multimeter was used to check for a constant, stable current across the surface of the fabric.

A third example is for the testing bacterial response to fabric. The same methods were used as in the first example, except the circuit was constructed with fabric squares rather than aluminum strips. Timed trials were run at five minutes, ten minutes, and fifteen minutes.

A fourth example is for the testing response of bacteria on chicken breast tissue to fabric. The same methods were used as in the third example, except the bacteria were added to the surface of chicken breast tissue. The fabric was held to the surface of the chicken breast tissue (both with and without a current carried across the fabric) in order to demonstrate the effectiveness of our design in a model that more closely simulates the surface of human skin.

A fifth example is for the testing bacterial response to the food preparation surface (wooden). The same methods were used as in the first example, except stainless steel wires were attached directly to the surface of a bamboo cutting board via hot glue. The surface was wetted in 50 gram/liter NaCl solution, which served as the medium to carry the current across the cutting board. 200 μL samples of bacteria suspensions were added either to the food preparation surface or to the surface of chicken breast tissue which was directly contacted with the food preparation surface. Both AC and DC currents were tested.

A sixth example is for the testing bacterial response to the food preparation surface (plastic). The same methods were used as in the fifth example, except the food preparation surface was composed of a plastic material which was treated to be hydrophilic and designed to hold water within and on top of itself. Stainless steel electrodes were attached through grooves that were manufactured into the cutting board. Both AC and DC currents were tested.

A seventh example is for the testing bacterial response to the fabric ex vivo on human skin. The same methods were used as in the third example, except *Bacillus subtilis* bacteria were first culture of a human face and used during experiments.

For the results of the examples, during the 24-hour electrification trials with aluminum strips, some growth was observed on the unelectrified controls but no growth on the electrified strips. In order to verify that the current caused the drop in bacterial viability, time dependent electrification experiments were performed. A minor reduction in colony formation was observed after five minutes, growing to a 56% reduction in viable colonies relative to the control after ten minutes.

Three different time trial conditions run with the conductive fabric. For this experiment, three different surfaces were electrified for five, ten, and fifteen minutes, respectively. As a control, three surfaces were simultaneously run, however, without treatment. From the data, the effects of treatment can be appreciated on bacterial viability; in particular, a significant decrease in bacterial surface area is seen as treatment time increases. Another observation lies within the control plates, and it is specifically observed that longer exposure to the fabric surface also reduces bacterial viability. Comparing the surface area covered in both cases, however, clearly reveals that surface electrification is a more efficient and effective method of sterilizing than relying on the antiseptic properties of silver alone.

In conclusion, the present invention provides a novel method of conferring antimicrobial and wound healing properties onto surfaces. The antimicrobial and wound healing properties arise from the generation of a uniform current across the surface by an attached power source. The surface is rendered conductive by means such as impregnating a woven or nonwoven fabric with conductive metal nanoparticles, blending with conductive polymers, wetting the surface between electrodes or any other method that confers conductivity. The power source, through an integrated circuit scheme, delivers a voltage that generates a constant current. Applications for these surfaces include use as household and clinical bed sheets, bed pads, blankets, medical gauze, pillowcases, and food preparation surfaces.

Although the invention has been explained in relation to its preferred embodiment, it is to be understood that many other possible modifications and variations can be made without departing from the spirit and scope of the invention as hereinafter claimed.

What is claimed is:

1. An electrification system for preventing transmission of pathogens by dermal contact comprising:
a skin-bracing object;
a power supply;
at least one resistor;
a first electrical connector;
a second electrical connector;
a first electrical terminal;
a second electrical terminal;
at least one first insulative rivet;
at least one second insulative rivet;
the skin-bracing object comprising an object body and a conductive feature;
the conductive feature being integrated into at least one specific surface of the object body;
the at least one resistor being mounted onto the object body;
the conductive feature, the resistor, and the power supply being electrically connected in series to each other as a closed circuit;
the power supply being configured to electrify pathogens in physical contact with the at least one specific surface by applying a specified current through the conductive feature;
the specified current being less than a current threshold of human sensitivity;
the at least one resistor and the conductive feature being electrically wired to the first electrical connector;
the power supply being electrically wired to the second electrical connector;
the first electrical connector being detachably and electrically engaged to the second electrical connector;
the first electrical terminal and the second electrical terminal being mounted onto the object body;
the first electrical terminal and the second electrical terminal being positioned opposite to each other across the at least one specific surface;
the at least one resistor being electrically connected to the conductive feature through the first electrical terminal;
the power supply being electrically connected to the conductive feature through the second electrical terminal;
the first electrical terminal being pressed against the conductive feature by the at least one first insulative rivet;
the second electrical terminal being pressed against the conductive feature by the at least one second insulative rivet;
the first electrical terminal and the second electrical terminal being a pair of exposed parallel wires;
the pair of exposed parallel wires being configured to prevent electrical arcing between each other by being positioned offset enough from each other;
the pair of exposed parallel wires being electrically connected to each other through the conductive feature;
the pair of exposed parallel wires being configured to apply a constant uniform electrical current across the conductive feature;
the object body being made of a textile; and
the first electrical terminal and the second electrical terminal being embedded into seams of the textile.

2. The electrification system for preventing transmission of pathogens by dermal contact as claimed in claim 1, wherein the object body is selected from a group consisting of: a pillowcase, a bed sheet, a bed pad, a blanket, a piece of medical gauze, a face mask, and a set of medical scrubs.

3. The electrification system for preventing transmission of pathogens by dermal contact as claimed in claim 1, wherein the conductive feature is a plurality of conductive fibers.

4. The electrification system for preventing transmission of pathogens by dermal contact as claimed in claim 1, wherein the conductive feature is a blend of conductive fibers and insulative fibers.

5. The electrification system for preventing transmission of pathogens by dermal contact as claimed in claim 1, wherein the conductive feature comprises a plurality of insulative fibers with conductive nanoparticles, and wherein the conductive nanoparticles are impregnated along each of the plurality of insulative fibers.

6. The electrification system for preventing transmission of pathogens by dermal contact as claimed in claim 5, wherein the plurality of insulative fibers is made of cotton, and wherein the conductive nanoparticles are made of silver.

7. The electrification system for preventing transmission of pathogens by dermal contact as claimed in claim 5, wherein the conductive nanoparticles are 33 percentage by weight (wt. %) of the conductive feature.

8. The electrification system for preventing transmission of pathogens by dermal contact as claimed in claim 1, wherein the conductive feature is a plurality of insulative fibers with a conductive surface treatment, and wherein the conductive surface treatment is applied to each of the plurality of insulative fibers.

9. The electrification system for preventing transmission of pathogens by dermal contact as claimed in claim 1, wherein the power supply is configured to apply the specified current as an alternating current (AC).

10. The electrification system for preventing transmission of pathogens by dermal contact as claimed in claim 9, wherein a frequency of the AC is approximately 1.8 Hertz (Hz).

11. The electrification system for preventing transmission of pathogens by dermal contact as claimed in claim 1, wherein the power supply is configured to apply the specified current as a pulsed direct current (DC).

12. The electrification system for preventing transmission of pathogens by dermal contact as claimed in claim 11, wherein a frequency of the pulsed DC is approximately 1.8 Hertz (Hz).

13. The electrification system for preventing transmission of pathogens by dermal contact as claimed in claim 1, wherein the current threshold of human sensitivity is approximately 50 milliamperes (mA).

14. The electrification system for preventing transmission of pathogens by dermal contact as claimed in claim 1, wherein the specified current is greater than 200 nanoamperes (nA).

15. The electrification system for preventing transmission of pathogens by dermal contact as claimed in claim 1, wherein the first electrical connector is a pair of banana plugs, and the second electrical connector is a female connector.

* * * * *